(12) United States Patent
Brodnick (10) Patent No.: US 6,351,664 B1
(45) Date of Patent: Feb. 26, 2002

(54) METHOD OF REMOVING SIGNAL INTERFERENCE FROM SAMPLED DATA AND APPARATUS FOR EFFECTING THE SAME

(75) Inventor: Don Brodnick, Cedarburg, WI (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/439,712

(22) Filed: Nov. 12, 1999

(51) Int. Cl.$^7$ .................................... A61B 5/0402
(52) U.S. Cl. ........................................ 600/509
(58) Field of Search ........................... 600/509

(56) References Cited

U.S. PATENT DOCUMENTS

| | | | |
|---|---|---|---|
| 4,408,615 A | 10/1983 | Grossman | 128/696 |
| 4,436,093 A | 3/1984 | Belt | 128/419 |
| 4,585,001 A | 4/1986 | Belt | 128/419 |
| 4,622,526 A | 11/1986 | Schneider et al. | 333/181 |
| 4,667,159 A | 5/1987 | Hodsoll, Jr. et al. | 324/309 |
| 4,939,473 A | 7/1990 | Eno | 328/167 |
| 5,051,963 A | 9/1991 | Linville, Jr. et al. | 367/46 |
| 5,188,177 A | 2/1993 | Curry | 166/297 |
| 5,208,837 A | 5/1993 | Richey | 375/103 |
| 5,278,777 A | 1/1994 | Cummins | 364/574 |
| 5,297,557 A | 3/1994 | Reichl | 128/707 |
| 5,318,036 A | 6/1994 | Arand et al. | 128/696 |
| 5,474,079 A | 12/1995 | Brodnick et al. | 128/711 |
| 5,687,735 A | 11/1997 | Forbes et al. | 128/696 |
| 5,699,045 A | 12/1997 | Frederick et al. | 340/551 |
| 5,903,615 A | 5/1999 | Thomson et al. | 375/346 |

OTHER PUBLICATIONS

Widrow, et al., "Adaptive Noise Cancelling: Principals and Applications," Proceedings of the IEEE, vol. 63, No. 12, Dec. 1975, pp. 1692–1716.

*Primary Examiner*—W. Kamm
(74) *Attorney, Agent, or Firm*—Michael Best & Friedrich LLP (57) ABSTRACT

A method and apparatus that separates an interference signal from a sampled input signal is provided. The method and apparatus approximates the frequency, phase and amplitude of the interference signal through an optional reverse direction learning process and then separates that portion of the interference signal overlapped or combined with a sample of the input signal. The signals can be separated by generating a second signal of suitable approximation in frequency, amplitude and phase with the interference signal and then subtracting a sample of that signal from the sampled input signal. The second signal frequency and amplitude/phase may be derived through an iterative process that measures the amplitude of the interference signal and the phase angle between the second signal and an output signal and then adjusts the frequency and amplitude of the second signal based, in part, on these measurements until the second signal substantially matches the interference signal. If desired, the processing method and apparatus may be applied to a digitized sampled waveforms and can operate at any sample frequency.

36 Claims, 5 Drawing Sheets

METHOD OF REMOVING SIGNAL INTERFERENCE FROM SAMPLED DATA AND APPARATUS FOR EFFECTING THE SAME

BACKGROUND OF THE INVENTION

The present invention relates to interference cancellation, and more particularly, to techniques for canceling periodic interference from sampled data.

Data sampled by an electronic device may include noise from the source supplying power to the device. In order to use the data, the noise often must first be removed.

An electrocardiograph or ECG machine is one example of a device that can be susceptible to power supply interference. Electrocardiographs are generally powered by standard electric power, which can be delivered as a sinusoid, at a frequency of sixty-hertz in the United States and Canada and fifty-hertz in Europe and other countries. While power is ideally delivered at a frequency of 50 or 60 Hz (the "nominal frequency"), the frequency may also vary from between approximately 40 and 60 Hz, depending upon load and other factors. It is within this frequency range that the power source noise can interfere with electrocardiograph operation.

Known devices that mitigate power supply interference, such as power source filters, for example, are typically set to filter everything but the frequency of interest, and are not capable of learning and eliminating power supply interference if the frequency of interference is different from the frequency setting of the filter. This inability to filter an interference signal having a changing frequency can pose significant risks when treating heart conditions and heart failures.

While the invention is described below in the context of an electrocardiograph, it should be understood that the invention is equally applicable to any electronic device that samples data.

SUMMARY OF THE INVENTION

The invention mitigates the above-described problems by providing a processing apparatus and a method that removes a periodic interference signal, even if it has a changing frequency or a frequency different from the nominal frequency, from a desired sampled signal. The invention removes signal interference through frequency hunting and signal separation.

More specifically, the present invention provides an apparatus for and a method of conditioning a signal, which signal includes a desired signal or "signal of interest" overlapped or combined with an interference signal of unknown frequency, amplitude, and phase. Preferably, the interference signal is a periodic signal, such as a sinusoidal signal like a power-line or a power-supply signal, for example.

In one aspect of the invention, the method approximates the frequency and amplitude of the interference signal through reverse direction filtering before separating the interference signal from the input signal. The approximation preferably estimates the frequency and amplitude of the interference signal using a control function or algorithm, such as a "bang—bang" algorithm, a "piece-wise" linear (a.k.a. "linear within limits") control function, or a sigmoid control function.

In another aspect of the invention, the method extracts a sample of the interference signal from a sample of the input signal through signal processing. In one exemplary embodiment, a second signal of suitable approximation in frequency and amplitude to the interference signal is sampled and that sample is then subtracted from an input signal sample to separate that portion of the interference signal that was overlapped or combined with the sample of the desired signal. The second signal frequency and amplitude may be derived from an iterative process that measures the amplitude of the interference signal and the phase angle between the interference signal and an output signal and then adjusts the frequency and gain of the second signal based, in part, on these measurements until the second signal substantially matches the interference signal.

In yet another aspect of the invention, the method removes the interference signal through filtering. In one exemplary embodiment, an active tunable notch filter is used to attenuate the interference signal. By actively identifying and tracking the frequency of the interference signal, the embodiment positions a filter null at the interference signal frequency. Although the exemplary embodiments describes a notch filter, the invention may use one or more filters that are capable of rejecting interfering signals in a frequency range such as on the order of two to twenty hertz, with a twenty hertz frequency range being the preferred range.

The disclosed methods can be implemented through software, analog, or digital circuitry or by any combination of these technologies. Preferably, when a reverse direction learning technique is implemented in at least a partially digital embodiment, the method processes the input signal in a reverse time direction (i.e. processing data from the last sample acquired to the first sample acquired within the data window) in order to learn the frequency, phase and amplitude of the interference signal prior to generating a filtered output. Stated differently, the learning of the frequency, phase and amplitude is done in the reverse direction (i.e., looking backward at already acquired data), while the filtering proceeds in the forward direction.

It is an advantage to provide a method of filtering power line interference from a signal of interest which method is not constrained to signals in which the frequency of the interference signal is constant or known in advance.

It is another advantage to provide a filtering method that is not limited to a specific sampling rate.

These features as well as other advantages of the invention will become apparent upon consideration of the following detailed description and accompanying drawings of the embodiments of the invention described below.

DETAILED DESCRIPTION

Figure 1:
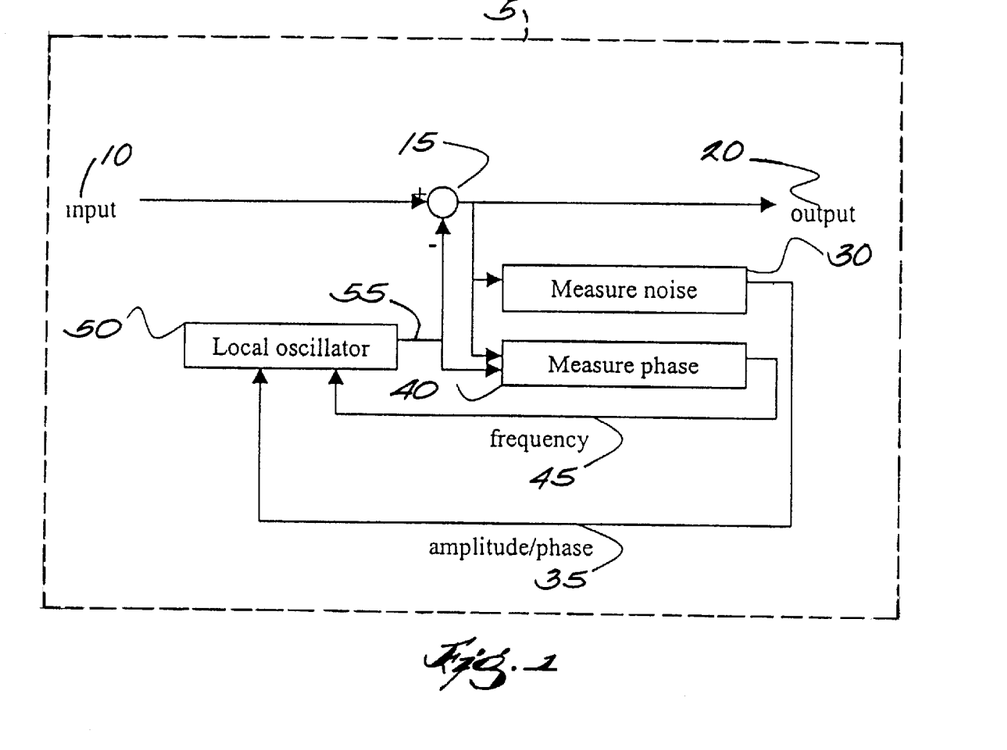
FIG. 1 is a schematic diagram of an electrocardiograph including a filter embodying the invention.

FIG. 1 schematically illustrates an electrocardiograph 5 embodying the invention. While the invention can be employed in any device sensitive to electrical interference, in the preferred embodiment the apparatus is an electrocardiogram machine having a filter that employs a method to remove interference from a signal of interest such as an electrocardiogram signal. Although the following exemplary embodiments are described in the context of an electrocardiogram machine that samples ten second periods of a time-varying signal at a rate of two hundred and fifty samples per second, the invention may also be applied to other machines or devices and other sampling systems, including systems having different sampling rates.

The electrocardiograph 5 conditions an input signal 10, which in the preferred embodiment is an electrocardiogram ("ECG") signal. The ECG signal comprises a desired signal overlapped or combined with an interference signal of unknown frequency, amplitude, and phase. Although it is understood that the interference signal is any unpredictable or undesirable signal(s), or changes in signal(s) that mask desired information in an input signal, for the purposes of explanation, the interference signal described with the exemplary embodiments is a periodic signal such as a sinusoid signal having a frequency within the range of about forty two to sixty two hertz.

As shown in FIG. 1, the input 10 to the electrocardiogram machine 5 is connected to a summing node 15. The summing node 15 may be either a circuit-based node or a software based node. The summing node 15 produces output signal 20.

Also shown in FIG. 1 are a pair of measuring circuits 30 and 40 connected to the output of the summing node 15. Measuring circuits 30 and 40 are connected to an oscillator circuit 50 that generates an oscillating signal 55 (shown in FIG. 2) of suitable approximation to the undesired interference signal. Preferably, the frequency, phase, and amplitude of the oscillating signal 55 substantially matches the frequency, phase, and amplitude of the interference signal, such that when the oscillating signal 55 is subtracted from the input signal 10, the interference signal is substantially eliminated from the input signal. Alternatively, the oscillating signal 55 may be shifted one hundred and eighty degrees out of phase with the interference signal such that when the oscillating signal 55 is added to the input signal 10, the interference signal is substantially eliminated from the input signal.

Measuring circuits 30 and 40 generate feedback signals 35 and 45, respectively, that represent the level of the noise in the output signal and the phase difference between the output signal and the oscillating signal 55. The feedback signals 35 and 45 adjust the amplitude and phase of the oscillating signal 55 so that the oscillating signal 55 is substantially similar in amplitude and phase to the interference signal. Although the exemplary embodiment of FIG. 1 illustrates a pair of measuring circuits 30 and 40 that generate feedback signals 35 and 45, a single circuit or software module can also be used to generate one or more feedback signals that, in part, adjust the operation of the oscillator circuit 50.

Figure 2:
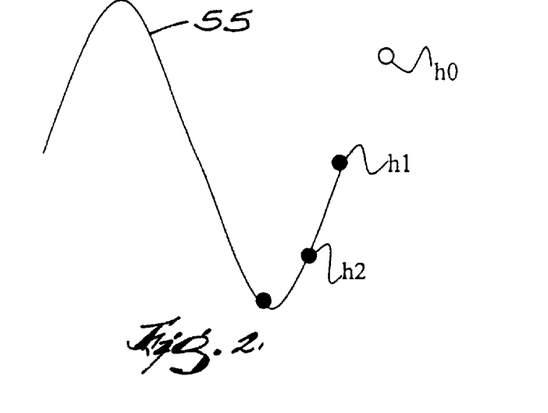
FIG. 2 is a graphical illustration of the oscillation signal of FIG. 1.

Equation 1 describes the oscillator signal 55 illustrated in FIG. 2.

$$2 \cdot \cos(\beta) \cdot \sin(\alpha) = \sin(\alpha-\beta) + \sin(\alpha+\beta) \quad \text{Equation 1}$$

Equation 1 predicts the position of a point or a sample of a sine wave given the value of two other points or samples. For the purpose of explanation, a current sample is assigned a sample subscript of zero (where "$_0$" indicates that the output is the most recently selected sample). Samples selected earlier in time are assigned higher subscripts that correlate to their respective sampling times.

$\beta$, which is the angle formed between two successive samples gathered from a single cycle of the interference signal, can be written as Equation 2 just as the other trigonometric expressions that comprise Equation 1 can be written in terms of sample variables $h_0$, $h_1$, and $h_2$, respectively.

$$\beta = 2 \cdot \pi \cdot F_j / \text{Number of Samples Per Second} \quad \text{Equation 2}$$

$$h_0 = \sin(\alpha+\beta) \quad \text{Equation 3}$$

$$h_1 = \sin(\alpha) \quad \text{Equation 4}$$

$$h_2 = \sin(\alpha-\beta) \quad \text{Equation 5}$$

Substituting Equations 2–5 into Equation 1 yields Equation 6

$$h_0 = 2 \cdot \cos(\beta) \cdot h_1 - h_2 \quad \text{Equation 6}$$

On the basis of Equation 6, a successive interference signal sample can be predicted from two previously known samples of the interference signal. While the invention is not limited to a sinusoid function, Equation 6 predicts the successive interference signal sample of a sinusoid of constant amplitude or a sinusoid of exponentially increasing or decreasing amplitude.

Preferably, the circuit shown in FIG. 1 systematically identifies or "hunts" for the frequency of the interference signal ($F_j$) so that the interference signal may be eliminated or substantially decreased in intensity from an input sample by attenuating the interference signal at its transmitting frequency. A tunable notch filter, for example, makes it possible for some of the exemplary embodiments to attenuate or eliminate one or more interfering signals that occur near the notch frequency from the input signal.

Figure 3:
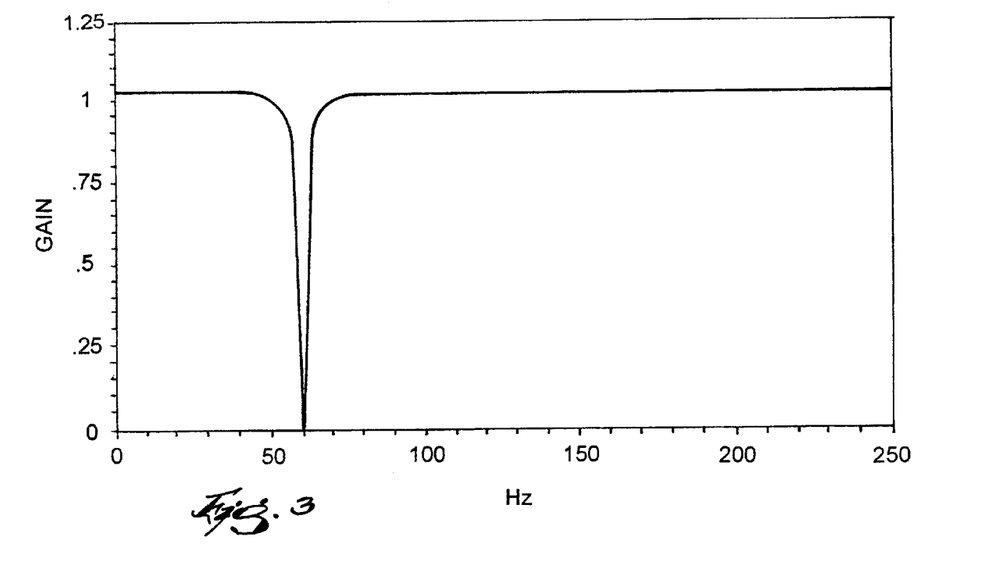
FIG. 3 is a magnitude response of a notch filter.

FIG. 3 illustrates a filter null or stop band of an active tunable notch filter tuned to approximately sixty hertz. At sixty hertz there is significant signal attenuation, with less signal attenuation occurring between the frequency band bounded by about fifty and seventy hertz. Accordingly, power line noise occurring at approximately sixty hertz is substantially dampened out.

Figure 4:
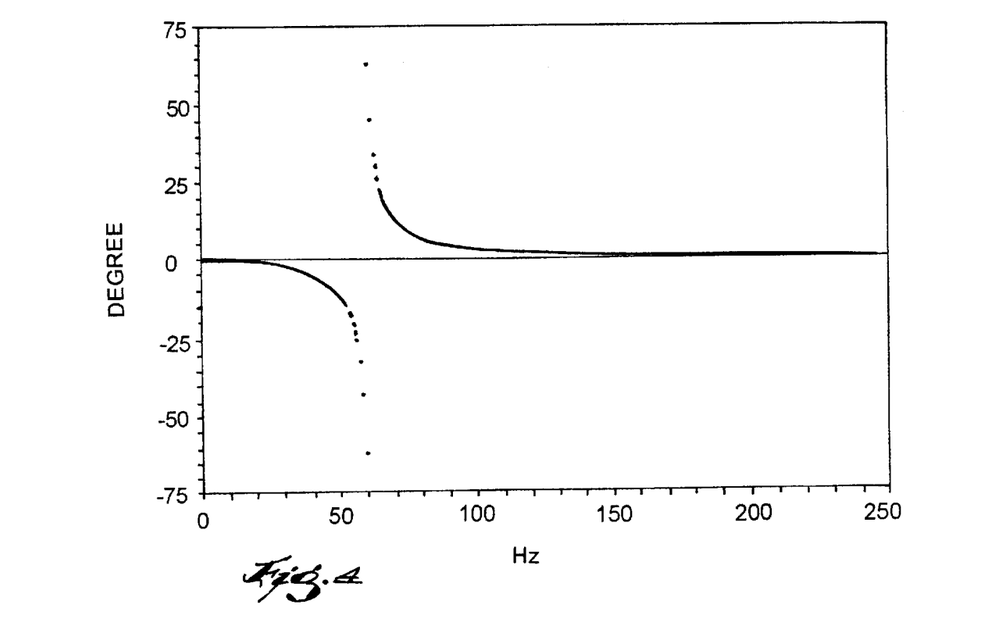
FIG. 4 is a phase response of the notch filter of FIG. 3.

As shown in FIG. 4, the notch filter has a negative phase response for frequencies less than sixty hertz (the notch frequency) and has a positive phase response for frequencies greater than the notch frequency. The illustrated phase response also has a one hundred and eighty degree phase shift between the fifty-ninth and sixty-first hertz frequency band (i.e. from a negative ninety degrees to a positive ninety degrees).

By using an active tunable notch filter in one exemplary embodiment, it is possible for the electrocardiograph 5 or other device to maintain a filter null at the interference frequency even when the frequency of the interference signal is changing or unknown. In view of this fact, a cross or vector product can be used to identify and track the phase of the interference signal go that the filter null effectively eliminates the interference signal frequency from the input signal. Of course, other known means of identifying and tracking the phase of an electrical signal are within the scope of the invention.

In one exemplary embodiment, the cross product of the input signal 10 and the oscillation signal 55 is used to identify the phase of the interference signal. In other exemplary embodiments, the cross products of the input 10 and output signal 20, and the output 20 and oscillation signal 55 are used, respectively.

Assuming that the samples, written below as Equations 7 through 10, describe the magnitude and direction of the interference signal and the oscillation signal 55, respectively, $y_0$=current output signal sample   Equation 7

$y_1$=previous output signal sample   Equation 8

$h_0$=current oscillation signal sample   Equation 9

$h_1$=previous oscillation signal sample   Equation 10 then the phase angle formed between the interference signal and the oscillation signal 32 can be written as Equation 11.

$$\text{phase} = (y0 \cdot h1) - (h0 \cdot y1) \quad \text{Equation 11}$$

Adjustments in the phase and the amplitude of the oscillator signal 55 occur by making small incremental step changes to the ho variable of Equation 6. These changes ensure that the oscillation signal 55 matches and tracks the frequency and the amplitude/phase of the interference signal. Because changes to the ho variable are limited to small incremental changes, transient or impulse input signals will not alter the oscillation signal 55 proportionately. In the context of an electrocardiograph, the range of change in the ho variable may be scaled to a fraction of a predetermined value, such as a fraction of the voltage of a specific bit in a digital embodiment. Under this control, the electrocardiogram machine will not produce an observable response to an input of short duration like pacemaker spikes or to the QRS complex of an ECG signal.

As those of ordinary skill in the art will appreciate, the invention may be implemented through integrated or discrete logic or through software. The variables and process steps of one exemplary embodiment that tracks the amplitude/phase and frequency of the interference signal and then subtracts a sample of a signal of suitable approximation to the interference signal from a sample of the input signal are disclosed in Table 1.

TABLE 1

| | | |
|---|---|---|
| 100 | $x_0$ | current input sample |
| 105 | $h_0, h_1, h_2$ | current and two previous oscillator samples |
| 110 | $y_0, y_1$ | current and previous output samples |
| 115 | Phase | phase measurement |
| 120 | $f_c$ | oscillator coefficient |
| 125 | $d_0$ | Noise measurement (first difference) |
| 130 | $h_0 = f_c * h_1 - h_2$ | propagate new oscillator sample |
| 135 | $y_0 = x_0 - h_0$ | summing node: input minus oscillation signal |
| 140 | phase = $y_0 * h_1 - h_0 * y_1$ | Phase measurement by cross product |
| 145 | if (phase < 0) $f_c$ -= FREQBUMP else $f_c$ += FREQBUMP | frequency adjustment of oscillator coefficient |
| 150 | $d_0 = y_0 - y_1$ | first difference estimate of interference in output |
| 155 | if ($d_0$ < 0) $h_0$ -= AMPBUMP else $h_0$ += AMPBUMP | Fixed amplitude adjustments avoid ringing |
| 160 | $h_2 = h_1$ | shift oscillator samples |
| 165 | $h_1 = h_0$ | shift oscillator samples |
| 170 | $y_1 = y_0$ | shift output samples |
| 175 | Return to step 130 | process is repeated |

Steps 100 through 125 define the sample variables of the invention.

At step 130, the oscillator sample is derived by subtracting a previous sample of the oscillator signal from the product of the oscillator coefficient and the current sample of the oscillation signal.

At step 135 the current sample of the interference signal is subtracted from the current sample of the input signal. The difference is a sample of the desired information.

At step 140 the phase of the interference signal is measured by the cross product of samples of the interference signal and samples of the output signal.

At step 145 the oscillator coefficient is adjusted according to a comparison between the phase of the interference signal and a constant such as zero. The polarity of the phase of the interference signal determines whether the oscillator coefficient is increased or decreased by the predetermined value "FREQBUMP."

At step 150 the current output sample is compared to the previous output sample to estimate the interference signal remaining in the output signal.

At step 155 the amplitude of the current sample is adjusted by the predetermined value "AMPBUMP."

At steps 160 through 175 the oscillator samples and output samples are transferred to variables having higher subscripts.

The process then repeats at step 175.

Figure 7:
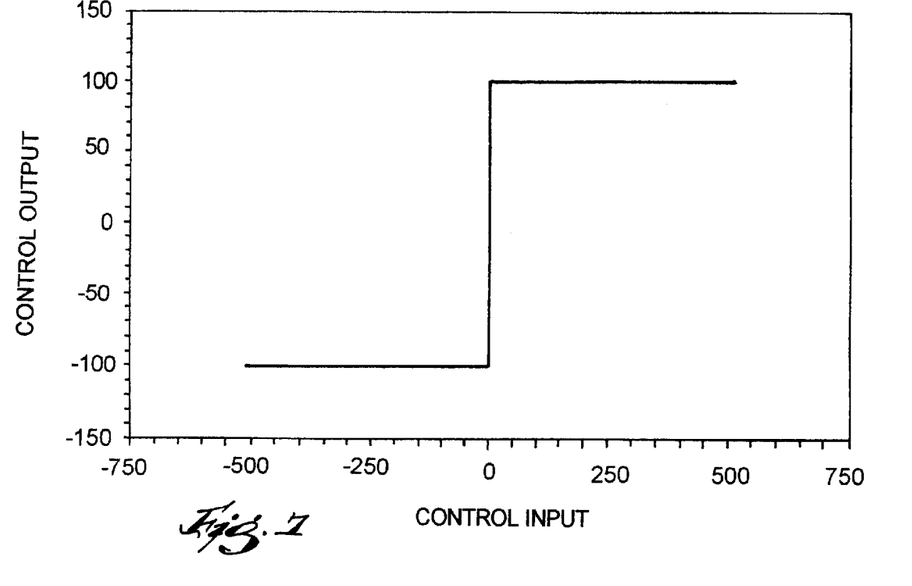
FIG. 7 illustrates the local oscillator control inputs of the filter of FIG. 1 employing a bang—bang control transfer function.

From the foregoing description and accompanying details provided in Table 1, it should be apparent that the variables "FREQBUMP" and "AMPBUMP" adjust the oscillator coefficient ("$f_c$" at step 145) and the next oscillator sample ("$h_0$" at step 155 but assigned to "$h_1$" at step 165) even when the phase ("phase") and the first difference ("$d_0$") are zero. These adjustments occur because the electrocardiograph 5 employs a bang—bang control algorithm for non-linear systems as is graphically shown in FIG. 7. The bang—bang control algorithm continuously adjusts the oscillator signal modifying the frequency and phase of the oscillator signal to approximate the interference signal. In the above-described exemplary embodiment, the function converts the noise measurement into a step adjustment of the oscillator gain, and converts the phase measurement into a step adjustment of the oscillator frequency.

Figure 8:
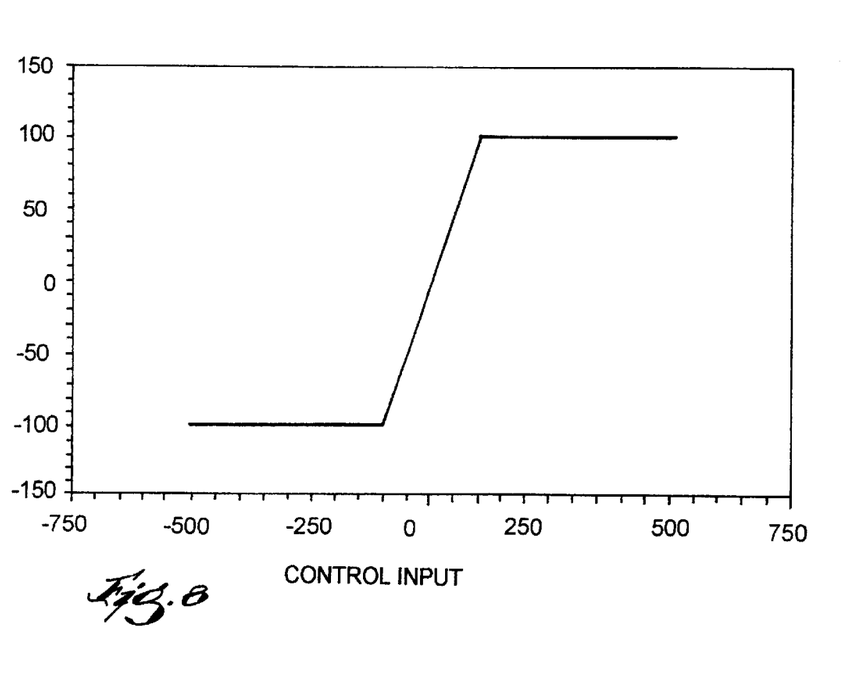
FIG. 8 illustrates the local oscillator control inputs of the filter of FIG. 1 employing a piece-wise linear control transfer function.
Figure 9:
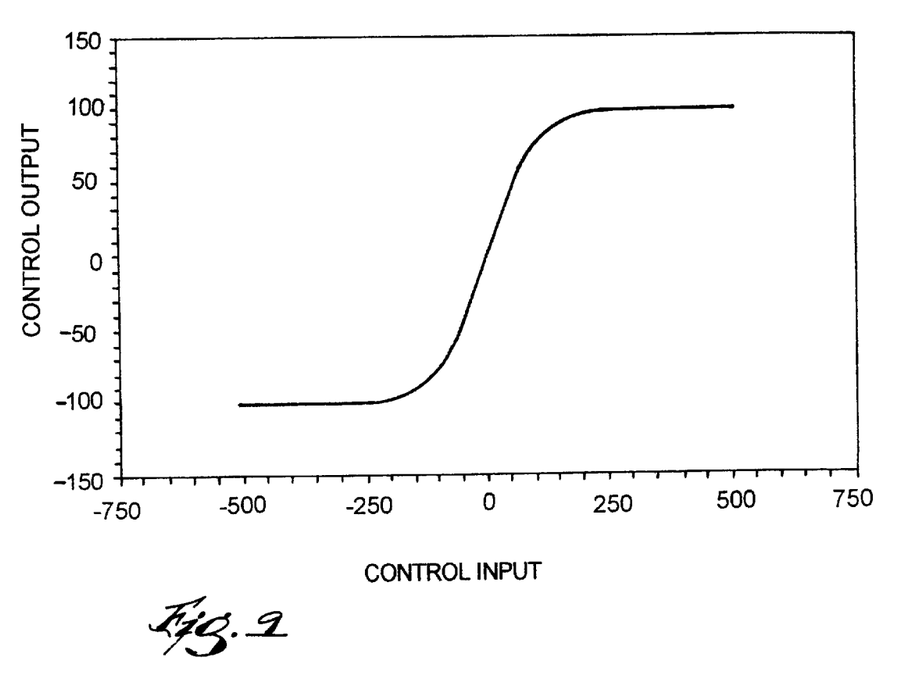
FIG. 9 illustrates the local oscillator control inputs of the filter of FIG. 1 employing a sigmoid control transfer function.

The above-described process is not limited to a specific control algorithm. Any function known to those of ordinary skill in the art, such as a piece-wise linear control algorithm as shown in FIG. 8, or as a sigmoid function as shown in FIG. 9, for example, may also be used.

Using a piece-wise linear control algorithm, the current oscillator sample and oscillator coefficient are subjected to smaller adjustments in comparison to the bang—bang control algorithm as the noise measurements of the output samples and phase measurements between samples of the oscillation and output signals approach zero. In those cases when the noise measurements and phase measurements are zero (i.e. when the amplitude/phase and frequency of the oscillating signal matches the interference signal), no adjustments in the oscillation coefficient and oscillation signal sample occurs.

Figure 5:
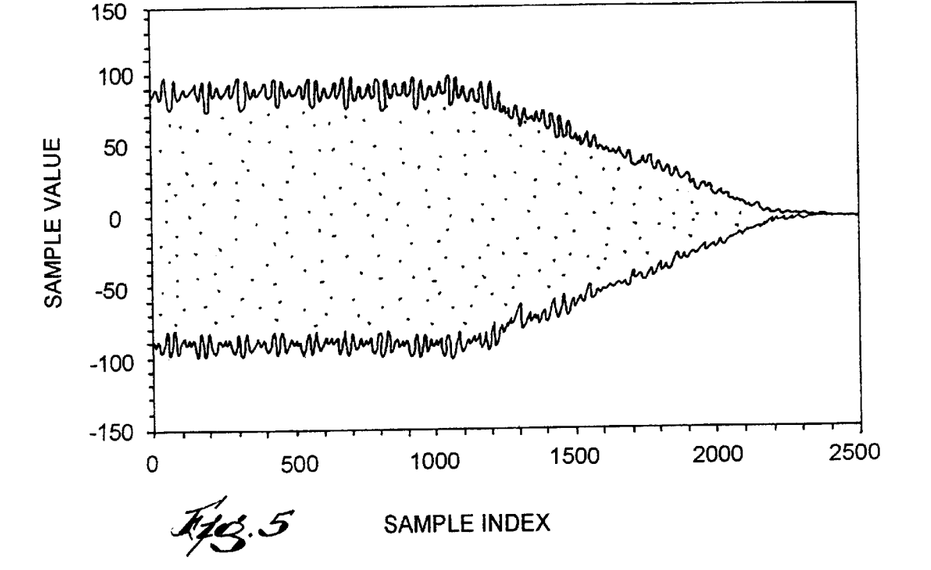
FIG. 5 is an exemplary response of the filter of FIG. 1 to an interference signal.

While the disclosed embodiments may be initialized at any frequency, the application shown in FIG. 5 initialized the oscillator circuit at fifty-two hertz and modeled the interference signal at forty-two hertz. In this application, the electrocardiograph identifies the interference signal frequency in about five seconds. Preferably, the electrocardiograph adjusts the oscillator signal within about a ten hertz range within approximately five seconds.

Figure 6:
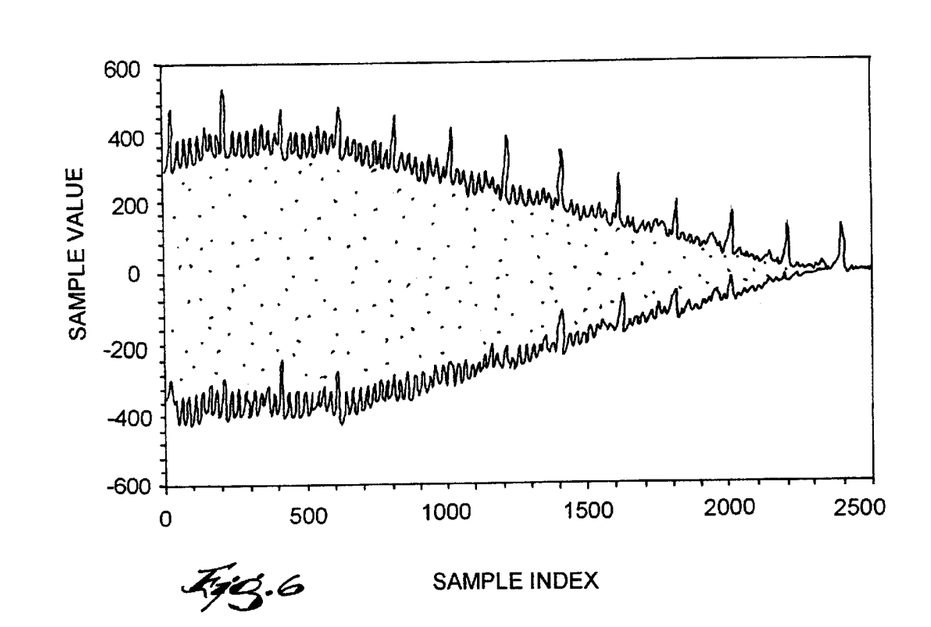
FIG. 6 is a view similar to FIG. 5 wherein the signal includes the desired signal overlapped or combined with the interference signal.

FIG. 6 illustrates a sixty hertz interference signal combined with an ECG signal reversed in time. As shown, after approximately two and one half seconds the amplitude of the interference signal begins to be reduced. Because the exemplary embodiment employs fixed amplitude adjustments, the amplitude of the interference signal is reduced at a constant rate. Alternatively, progressive and/or non-linear amplitude/phase and/or frequency adjustments can be used to attenuate the interference signals within the input samples.

In one embodiment, the electrocardiograph 5 acquires and stores in a buffer the digitized sampled waveform. The interference signal frequency, phase and amplitude are learned by the software or hardware method by processing samples from one end of the buffer to the other, preferably from the last acquired sample to the first acquired sample. This learning pass of the method does not produce output samples for storage or eventual use by the instrument. However, this learning pass does result in a known state of the interference signal at one end of the buffer, i.e., the end last processed. Then a second pass through the buffer can be made beginning from the end where the state of the interference signal is known, producing output samples substantially free from interference. The filtering pass will proceed in the opposite direction through the buffer of samples compared to the learning pass. The learning pass may proceed backward in time and the filtering pass forward in time, or alternatively, the learning pass may proceed forward in time and the filtering pass backward in time.

Persons of ordinary skill in the art will appreciate that the invention may also use forward filtering and can be implemented through software, random logic (i.e. gates, inverters, flip flops, etc.) or programmable logic (i.e. digital or signal processors) and conditioning components including analog-to-digital converters, for example. The samples may be stored in volatile or non-volatile memory or displayed on a CRT, an LCD, or other known display devices. Moreover, in any application, a plurality of filters embodying the invention may be used at the same time to remove interference at the harmonics of the fundamental frequency or frequency of interest.

It should be understood that the invention is not limited in its application to the details of the construction and the arrangements of the components set forth in the description or illustrated in the drawings. The invention is capable of other embodiments and of being practiced or being carried out in various ways. Also, it is to be understood that the phraseology and terminology used herein is for the purpose of description and should not be regarded as limiting.

What is claimed is:

1. A method for removing interference signals from a sampled signal comprising the steps of:
   sampling an input signal comprising a selected signal combined with an interference signal having a frequency and an amplitude;
   approximating the frequency, amplitude and phase of the interference signal; and
   separating the interference signal from the sampled input signal.

2. The method of claim 1 wherein the act of approximating uses an iterative reverse direction learning process.

3. The method of claim 1 further comprising the act of: generating a second signal of suitable approximation in frequency and amplitude to the interference signal.

4. The method of claim 3 wherein the separating act comprises subtracting a sample of the second signal from one of the samples of the input signal.

5. The method of claim 1 wherein the approximating act includes the act of estimating the frequency and amplitude of the interference signal using a bang—bang control algorithm.

6. The method of claim 1 wherein the approximating act includes the act of estimating the frequency and amplitude of the interference signal using a piece-wise linear control function.

7. The method of claim 1 wherein the approximating act includes the act of estimating the frequency and amplitude of the interference signal using a sigmoid control function.

8. The method of claim 1 wherein the approximating act includes the act of estimating the phase of the interference signal through a cross-product function.

9. The method of claim 1 wherein the approximating act comprises the acts of:
   generating a second signal;
   measuring a phase angle between samples of the selected signal and samples of the second signal;
   estimating the amplitude of a sample of the interference signal; and
   adjusting the frequency and amplitude and phase of the second signal to substantially match the interference signal.

10. The method of claim 9 wherein the separating act comprises the act of subtracting at least one sample of the second signal from the sampled input signal after the adjusting act.

11. The method of claim 9 wherein the selected signal is an output signal.

12. The method of claim 11 wherein the act of measuring the phase angle comprises calculating the cross product of the samples of the output signal and the second signal.

13. The method of claim 1 wherein the approximating act is an iterative process of estimating an amplitude of the interference signal and a phase angle between the interference signal and an output signal and adjusting the frequency and amplitude of the second signal based in part on these measurements until a sample of the second signal substantially matches a sample of the interference signal.

14. The method of claim 1 wherein the separating act comprises filtering a sample of the interference signal from a sample of the input signal.

15. The method of claim 14 wherein the filtering act uses a notch filter.

16. The method of claim 14 wherein the separating act comprises positioning a filter null of a notch filter at the frequency of the sample of the interference signal.

17. The method of claim 1 wherein the interference signal is a sinusoid.

18. A method for removing interference signals from selected electrocardiogram signals comprising the acts of:
   sampling an input signal comprising a selected electrocardiogram signal combined with a sinusoidal interference signal having a frequency and an amplitude;
   comparing successive samples of an output signal backward in time using a reverse direction learning process to measure frequency, amplitude and phase of the interference signal;
   generating a second signal of suitable approximation in frequency, amplitude and phase to the interference signal; and
   subtracting a sample of the second signal from one sample of the input signal.

19. The method of claim 18 wherein the generating act comprises the acts of:
(a) adjusting the amplitude and phase of the second signal by a predetermined amount if the amplitude and phase of the second signal is not substantially equal to the amplitude and phase of the interference signal:
(b) adjusting the frequency of the second signal by a predetermined amount if the frequency of the second signal is not substantially equal to the frequency of the interference signal; and then
(c) repeating acts b and c until the second signal is substantially equal in frequency, amplitude and phase to the interference signal.

20. The method of claim 18 wherein the subtracting act comprises shifting the sample of the second signal one hundred and eighty degrees out of phase with respect to the phase of the input signal and then adding the sample of the second signal to one sample of the input signal.

21. The method of claim 18 wherein the selected signal is an electrocardiogram signal.

22. The method of claim 18 wherein the comparing act includes the act of estimating the frequency and amplitude of the interference signal using a bang—bang control algorithm.

23. The method of claim 18 wherein the comparing act includes the act of estimating the frequency and amplitude of the interference signal using a piece-wise linear control function.

24. The method of claim 18 wherein the comparing act includes the act of estimating the frequency and amplitude of the interference signal using a sigmoid control function.

25. The method of claim 18 wherein the comparing act includes the act of estimating the phase of the interference signal through a cross-product function.

26. An apparatus for removing power line interference from a sampled signal, the apparatus comprising:
an input circuit tuned to receive an input signal, said input signal comprising a selected signal and an interference signal;
a detection circuit connected to the input circuit to approximate the frequency, amplitude and phase of the interference signal using a reverse direction learning process; and
a separating circuit coupled to the input circuit and the detection circuit to remove the interference signal from the input signal.

27. The apparatus of claim 26, wherein the detection circuit comprises a noise measuring circuit and a phase measuring circuit.

28. The apparatus of claim 26, wherein the detection circuit comprises an oscillator circuit that generates a signal of suitable approximation in frequency, amplitude and phase to the interference signal.

29. The apparatus of claim 28, wherein the detection circuit comprises a noise measuring circuit and a phase measuring circuit having a common input coupled to the separating circuit and having an output coupled to the oscillator circuit.

30. The apparatus of claim 26, wherein the separating circuit comprises a summing circuit.

31. An electrocardiograph including a filter for removing power line interference from a sampled electrocardiograph signal, the electrocardiograph comprising:
an input circuit tuned to receive an input signal comprising an electrocardiograph signal and an interference signal;
a detection circuit connected to the input circuit to approximate the frequency, amplitude and phase of the interference signal using a reverse direction learning process; and
a separating circuit coupled to the input circuit and the detection circuit to remove the interference signal from the input signal.

32. The electrocardiograph of claim 31, wherein the detection circuit comprises a noise measuring circuit and a phase measuring circuit.

33. The electrocardiograph of claim 31, wherein the detection circuit comprises an oscillator circuit that generates a signal of suitable approximation in frequency, amplitude and phase to the interference signal.

34. The electrocardiograph of claim 33, wherein the detection circuit comprises a noise measuring circuit and a phase measuring circuit having a common input coupled to the separating circuit and having an output coupled to the oscillator circuit.

35. The electrocardiograph of claim 31, wherein the separating circuit comprises a summing circuit.

36. The electrocardiograph of claim 31 wherein the detection circuit and the separating circuit comprise the filter, and wherein the electrocardiograph includes a plurality of like filters cascaded to independently reject the fundamental interference frequency and harmonics of the fundamental frequency.

* * * * *